United States Patent [19]

Anderson et al.

[11] Patent Number: 4,826,973
[45] Date of Patent: May 2, 1989

[54] DELTA FORM OF AZTREONAM AND PREPARATION THEREOF

[75] Inventors: Neal G. Anderson, Somerset; Carl F. Anderson, North Brunswick, both of N.J.

[73] Assignee: E. R. Squibb & Sons, Inc., Princeton, N.J.

[21] Appl. No.: 807,374

[22] Filed: Dec. 10, 1985

Related U.S. Application Data

[63] Continuation-in-part of Ser. No. 632,744, Jul. 20, 1984, abandoned, which is a continuation-in-part of Ser. No. 437,773, Oct. 29, 1982, abandoned.

[51] Int. Cl.$^4$ ............................................. C07D 417/12
[52] U.S. Cl. .................................................... 540/355
[58] Field of Search ......................................... 540/355

[56] References Cited

FOREIGN PATENT DOCUMENTS 70024 1/1983 European Pat. Off. .

Primary Examiner—Mark L. Berch
Attorney, Agent, or Firm—Burton Rodney

[57] ABSTRACT

The crystalline delta($\delta$)-form of [3S-[3$\alpha$(Z),-4$\beta$]]-3-[[(2-amino-4-thiazolyl) [(1-carboxy-1-methylethoxy)imino]acetyl]amino]-4-methyl-2-oxo-1-azetidinesulfonic acid is prepared.

12 Claims, No Drawings

DELTA FORM OF AZTREONAM AND PREPARATION THEREOF

REFERENCE TO OTHER APPLICATIONS

This application is a continuation-in-part of U.S. application Ser. No. 632,744, filed July 20, 1984, now which is a continuation-in-part of U.S. application Ser. No. 437,773, filed Oct. 29, 1982, now abandoned.

FIELD OF THE INVENTION

The present invention relates to a new crystalline, highly dense form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid, referred to as the δ(delta)-form of aztreonam, which has unique physical characteristics enabling it to be ideally suited for large-scale preparations of aztreonam.

BACKGROUND OF THE INVENTION

In U.S. patent application Ser. No. 226,562, filed Jan. 19, 1981, by Richard B. Sykes, et al., there is described a method for preparing the new antibacterial agent, [3S-[3α(Z)4β]]-3-[[(2-amino-4-thiazolyl)[(1-carboxy-1-methylethoxy)imino]acetyl]amino]-4-methyl-2-oxo-1-azetidinesulfonic acid, having the formula

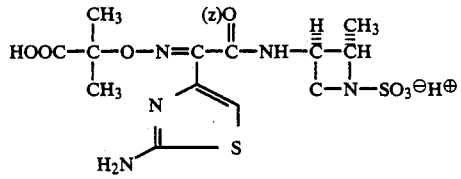

and hereinafter referred to also as aztreonam The compound so obtained is in the form of hydrated crystals, which have been designated as the α-form, which are relatively unstable.

In U.S. patent application Ser. No. 282,636, filed July 13, 1981, by David Floyd et al., there is described a method for recrystallizing the above-mentioned α-form of aztreonam from an anhydrous organic solvent to form the β-form of aztreonam. The β-form is anhydrous, substantially non-hygroscopic and more stable than the α-form.

DETAILED DESCRIPTION OF THE INVENTION

In accordance with the present invention, a new crystalline form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid is provided which is referred to hereinafter as the δ-form of aztreonam.

The δ-form of aztreonam is essentially a complex of aztreonam, methylene chloride ($CH_2Cl_2$) and water with a theoretical composition of 15.8% $CH_2Cl$ and 3.35% $H_2O$ on a weight basis. Typically, the δ-form will contain from about 16% by weight $CH_2Cl_2$ and from about 2.5 to about 4.5% by weight $H_2O$ as measured by gas chromatography and Karl Fischer titration, respectively.

The δ-form of aztreonam has excellent physical, bulk properties in that it is a dense, granular solid which may be separated from supernatant solvents very readily, such as by filtration and/or centrifugation. Isolation of the δ-form of aztreonam is easily facilitated so that further drying as by, for example, fluid bed drying or vacuum drying, is unnecessary, Thus, due to the unique physical properties of the δ-form of aztreonam, isolation time for production runs is appreciably reduced with the recovery of a substantially cleaner material especially in comparison to that required for the γ-form of aztreonam. Another attractive property of the δ-form of aztreonam is its excellent bulk stability, which is similar to that of the β-form, and will allow it to be stored in the δ-form before it is converted to the sterile β-form. In contrast, the poor stability of the α-form dictates speedy conversion to the sterile β-form.

The δ-form of aztreonam can be characterized as a stable, dense, crystalline, granular solid, exhibiting characteristic X-ray powder diffraction curves that distinguish it from the α-form, β-form and γ-form. The following is a listing of interplanar distances ('d') versus intensity (I) of the α-β, γ and δ forms the intensity being expressed as % of full scale (F.S.), where off-scale peaks are expressed as >100:

TABLE I

Typical X-Ray Powder Diffraction Patterns for α-, β-, γ- and δ-Forms of Aztreonam

| α-Form of Aztreonam | | β-Form of Aztreonam | | | | γ-Form of Aztreonam | | δ-Form of Aztreonam | |
|---|---|---|---|---|---|---|---|---|---|
| | | Sample I | | Sample II | | | | | |
| 'd' (Å) | I(% F.S.) | 'd' | I(% F.S.) | 'd' | I(% F.S.) | 'd' (Å) | I(% F.S.) | 'd' (Å) | I(% F.S.) |
| 3.2 | 7 | 3.18 | 40 | | | 3.22 | 34 | 3.24 | 11 |
| 3.26 | 34 | 3.23 | 58 | 3.21 | 29 | 3.42 | 16 | 3.27 | 33 |
| 3.32 | 25 | 3.35 | 35 | 3.32 | 18 | 3.58 | 72 | 3.36 | 13 |
| 3.43 | 60 | 3.43 | 35 | 3.43 | 16 | 3.71 | 47 | 3.44 | 14 |
| 3.67 | 28 | 3.5 | 5 | | | 3.81 | 21 | 3.53 | 82 |
| 3.74 | 35 | 3.62 | 60 | 3.60 | 32 | 4.02 | 56 | 3.62 | 13 |
| 3.90 | 32 | 3.72 | 45 | | | 4.22 | 21 | 3.69 | 27 |
| 3.98 | 25 | 3.8 | 60 | 3.78 | 39 | 4.57 | >100 | 3.75 | 38 |
| 4.22 | 21 | 3.87 | 10 | | | | (base peak) | 3.98 | 4 |
| 4.37 | 7 | 4.12 | >100 | 4.10 | >100 | 4.88 | 19 | 4.20 | 56 |
| 4.47 | 10 | 4.23 | >100 | 4.20 | >100 | 5.13 | 26 | 4.42 | 35 |
| 4.6 | 30 | 4.41 | 15 | 4.40 | 11 | 5.6 | 58 | 4.49 | 33 |
| 4.7 | 57 | 4.72 | >100 | 4.72 | >100 | 5.8 | >100 | 4.82 | 8 |
| 5.03 | 26 | 4.90 | 20 | 4.50 | 16 | 6.17 | 25 | 4.98 | 34 |
| 5.32 | 48 | 5.0 | 55 | 4.95 | 35 | 6.48 | 27 | 5.16 | 37 |
| 5.64 | 7 | 5.25 | >100 | 5.21 | >100 | 7.1 | 41 | 5.51 | 8 |
| 5.82 | 32 | 5.4 | 5 | | | 8.4 | 45 | 6.16 | 100 |
| 6.35 | 6 | 5.62 | 23 | 5.6 | 18 | 9.1 | 29 | 6.74 | 29 |
| 6.7 | 12 | 5.78 | 25 | 5.75 | 15 | | | 7.4 | 46 |
| 7.0 | >100 | 6.32 | 15 | 6.3 | 10 | | | 8.9 | 4 |
| 7.1 | 33 | 7.8 | >100 | 7.7 | >100 | | | | |
| 8.1 | 10 | 9.3 | 20 | 9.2 | 14 | | | | |

TABLE I-continued

Typical X-Ray Powder Diffraction Patterns for α-, β-, γ- and δ-Forms of Aztreonam

| α-Form of Aztreonam | | β-Form of Aztreonam | | | | γ-Form of Aztreonam | | δ-Form of Aztreonam | |
|---|---|---|---|---|---|---|---|---|---|
| | | Sample I | | Sample II | | | | | |
| 'd' (Å) | I(% F.S.) | 'd' | I(% F.S.) | 'd' | I(% F.S.) | 'd' (Å) | I(% F.S.) | 'd' (Å) | I(% F.S.) |
| 9.2 | 30 | 10.0 | 40 | 9.9 | 29 | | | | |
| 10.7 | 35 | | | | | | | | |
| 13.8 | 20 | | | | | | | | |
| 18.9 | >100 | | | | | | | | |

Note that the peak intensities may change subject to variation in sample preparation The δ-form of [3S-[3α(Z),4β]]-3-[[(2-amino-4-thiazolyl)[(1-carboxy-1-methylethoxy)imino]acetyl-]amino-4-methyl-2-oxo-1-azetidinesulfonic acid can also be distinguished from the α-form, β-form and γ-form as shown in the following Table:

TABLE II

Physical and Processing Properties of Crystalline Forms of [3S—[3α(Z),4β]]-3-[[(2-Amino-4-thiazolyl)-[(1-carboxy-1-methylethoxy)imino]acetyl]amino]-4-methyl-2-oxo-1-azetidinesulfonic Acid (Aztreonam)

| Property | α-Form | β-Form | γ-Form | δ-Form |
|---|---|---|---|---|
| Hydration | Hydrous (7–14% water) | Anhydrous (0–1% water) | 0–1% $H_2O$ | Hydrous (2.5–4.5% water) |
| Typical Solvation | 0–1% EtOH (fluid-bed dried) 7–8% EtOH (vacuum dried) | 2.5% EtOH | 0–1% EtOH | 9–16% $CH_2Cl_2$ |
| Crystallinity: | | | | |
| Microscopy | birefringement | birefringent | birefringent | birefringent |
| X-ray diffraction | crystalline (alpha-form) | crystalline (beta-form) | crystalline (gamma-form) | crystalline (delta-form) |
| [1]DSC, peak temperatures: | | | | |
| exotherm | 200° C. (decomp) | 238° (decomp) [when crystallized from absolute methanol] 228° (decomp) [when crystallized from absolute ethanol] | 228° C. (decomp) | 197,214° C. (decomp) |
| endotherm | 107° C. (dehydration) | none | none | 137° (desolvation) |
| Morphology | needles or rods | spiny fused spherulites | matted nails | spirally shingled surface |
| Infrared Spectra: (KBr disc) | very wide absorption band in the 3000–3600 $cm^{-1}$ region (characteristic of water); poorly resolved shoulder on the peak at 1650 $cm^{-1}$ (carbonyl region). | narrower band in the 3000–3600 $cm^{-1}$ region; well resolved shoulder on the peak at about 1780 $cm^{-1}$. | no striking difference from α-form, although the fingerprint regions differ | no striking difference between α-form, although the fingerprint regions differ |
| Density | low | high | low | high |
| Surface Area | high | low | high | low |
| Flowability | poor | good | poor | good |
| Intrinsic Dissolution Rate | slow | fast | fast | fast |
| Solid State Stability | poor | good | unknown | good |
| Ease of Manufacture (Aseptic Powder Blend) | poor | good | N.A. | N.A. |
| Drying Treatment Necessary After Isolation | appreciable | | appreciable | none to minimal |

[1]DSC - Differential Scanning Calorimetry

Because of its increased bulk stability, the δ-form of the compound is particularly well suited for use as an intermediate in preparing the β-form of [3S-[3α(Z),4β]]-3-[[(2-amino-4-thiazolyl)-[(1-carboxy-1-methylethoxy)imino]acetyl]amino]-4-methyl-2-oxo-1-azetidinesulfonic acid. The shelf life of the δ-form, because of its enhanced stability, is greater than that of the α-form, or for that matter simple salts of the compound, thereby permitting more prolonged storage prior to conversion to the β-form, without material decomposition. This is a meaningful advantage of the δ-form when utilized commercially.

The δ-form of aztreonam may be prepared by the acid-mediated solvolysis of [2S-[2α,3β(Z)]]-3-[[(2-amino-4-thiazolyl)-[[2-diphenylmethoxy)-1,1-dimethyl-2-oxoethoxy]imino]acetyl]amino]-2-methyl-4-oxo-1-azetidinesulfonic acid. The solvolysis may be carried out employing acids such as trifluoroacetic acid or trichloroacetic acid.

In one embodiment, the solvolysis is carried out by first dissolving the above 1-azetidinesulfonic acid in a chlorinated hydrocarbon solvent such as $CH_2Cl_2$ and then reacting the mixture with an acid such as trifluoroacetic acid or trichloroacetic acid. In another embodiment, the solvolysis is carried out by first dissolving the trifluoroacetic acid or trichloroacetic acid in a chlorinated hydrocarbon solvent such as $CH_2Cl_2$ and then reacting the mixture with the above 1-azetidinesulfonic acid.

Alternatively, the δ-form of aztreonam may be prepared by the recrystallization of the α-form of aztreonam by dissolving the α-form in an anhydrous organic polar solvent such as dimethylformamide or dimethylsulfoxide and adding a chlorinated hydrocarbon solvent such as CH$_2$Cl$_2$ thereto.

In still another embodiment, the δ-form of aztreonam may be prepared by dissolving the β-form of aztreonam in a solvent such as ethanol and water, cooling the solution to precipitate a solid, dissolving the solid in an organic polar solvent, such as dimethylformamide or dimethylsulfoxide, and then adding a chlorinated hydrocarbon solvent such as CH$_2$Cl$_2$ thereto.

The starting material [2S-[2α,3β(Z)]]-3-[[2-amino-4-thiazolyl][[2-(diphenylmethoxy)-1,1-dimethyl-2-oxoethoxy]imino]acetyl]amino]-2-methyl-4-oxo-1-azetidinesulfonic acid for use in preparing the δ-form of aztreonam can be prepared as described in the following Preparation A, in which all temperatures are in degrees Centigrade.

PREPARATION A

[2S-[2α,3β(Z)]]-3-[[(2-Amino-4-thiazolyl)-[[2-(diphenylmethoxy)-1,1-dimethyl-2-oxoethoxy]imino]acetyl]amino]-2-methyl-4-oxo-1-azetidinesulfonic acid A. (3S-trans)-3-Amino-4-methyl-2-oxo-1-azetidinesulfonic acid Under an atmosphere of nitrogen, a flask containing 500 ml of methanol was cooled to −5° C. (ice/brine) and 130 ml (excess) of thionyl chloride was added at such a rate as to maintain the reaction temperature between 0° and 10° C. After recooling to −5° C., 59.5 g of l-threonine was added and the mixture was allowed to reach room temperature and stirred for 16 hours. The mixture was concentrated and evacuated at 10$^{-1}$ torr for 2 hours to yield threonine, methyl ester, hydrochloride as a viscous oil. This material was used directly in the following step.

The crude threonine, methyl ester, hydrochloride was dissolved in 2.5 l of methanol and cooled at −5° C. (ice/brine). The solution was saturated with ammonia gas, the cooling bath was removed and the sealed vessel was allowed to stand for 3 days. After removing the bulk of the unreacted ammonia via aspirator, 100 g of sodium bicarbonate and 50 ml of water were added and the mixture was stipped to a viscous oil, namely, threonine amide.

The crude threonine amide (already containing the requisite amount of sodium bicarbonate) was diluted to a volume of 1 liter with water. To this rapidly stirring solution, 94 g (88 ml of 90% pure material) of benzyloxycarbonyl chloride was added as a solution in 80 ml of tetrahydrofuran over a 1 hours period. The reaction mixture was then stirred for an additional 16 hours and extracted with ethyl acetate (one 500 ml portion, two 250 ml portions). The combined extracts were dried over magnesium sulfate and concentrated. The crystalline residue was then dissolved in 250 ml of hot ethyl acetate and 300 ml of hexane was added followed by boiling until a clear solution was reacted. Cooling and filtration of the crystalline mass gave, after drying, 104 g of benzyloxycarbonylthreonine amide.

Under an atmosphere of argon, 100 g of benzyloxycarbonylthreonine amide was dissolved in 400 ml of anhydrous pyridine and cooled in an ice/salt bath. To this stirring solution, 36.8 ml (54.5 g) of methanesulfonyl chloride was added over a 15 minute period. After 2 hours of stirring an additional 0.3 equivalents of methanesulfonyl chloride was added. The reaction was then stirred for 1 hour and poured into a mixture of 1.5 l of ice and 2 l of water. The resulting slurry was stirred for about 30 minutes and filtered. Drying of the crude product at 60° C. for about 16 hours in a vacuum oven gave 109 g of benzyloxycarbonylthreonine amide, O-mesylate.

A solution of 2-picoline (17.8 ml) in 90 ml of methylene chloride was cooled to −5° C. (ice-brine) and chlorosulfonic acid (5.97 ml) was added at such a rate as to maintain the internal reaction temperature below 5° C. The resulting solution was added via canula, to a suspension of 7.56 g of benzyloxycarbonylthreonine amide, O-mesylate in 120 ml of methylene chloride. The resulting heterogeneous mixture was refluxed for about 16 hours yielding a clear solution. The solution was poured into 500 ml of pH 4.5 phosphate buffer (0.5M) and further diluted with 120 ml of methylene chloride. The separated organic layer was washed once with 100 ml of buffer solution and the combined aqueous phases were treated with 10.2 g of tetra-n-butyl-ammonium hydrogensulfate and extracted with methylene chloride (one 300 ml portion and two 150 ml portions). After drying the combined organic extracts over sodium sulfate, the solution was concentrated to yield 12.7 g of N-sulfonyl benzyloxycarbonylthreonine amide, O-mesylate, tetrabutylammonium salt.

A mixture consisting of 5.52 g of potassium carbonate in 20 ml of water and 160 ml of 1,2-dichloroethane was brought to reflux and 15.5 mmoles of N-sulfonyl benzyloxycarbonylthreonine amide, O-mesylate, tetrabutylammonium salt were added in 20 ml of 1,2-dichloroethane (20 ml used as a rinse). After refluxing for 30 minutes, the mixture was poured into a separatory funnel, diluted with 50 ml of water and 100 of methylene chloride and the phases split. The resulting organic phase was dried over sodium sulfate and concentrated to yield crude (3S-trans)-3-benzyloxycarbonylamino-4-methyl-2-oxo-1-azetidinesulfonic acid, tetrabutylammonium salt. The crude azetidinone was treated in 250 ml of ethanol with 0.8 g of 5%5 palladium on charcoal catalyst and hydrogen was bubbled through the solution. After 90 minutes the mixture was filtered through Celite with 50 ml of ethanol used as a rinse.

The addition of 1.2 ml of formic acid to this solution caused an immediate precipitation of the title zwitterion which was filtered after stirring for 1 hour to yield, after drying at 10$^{-1}$ torr for 1 hour, 1.1 g of (3S-trans)-3-amino-4-methyl-2-oxo-1-azetidinesulfonic acod. A second crop of product was obtained upon concentration of the filtrate and addition of more formic acid to give 1.3 g of the zwitterion.

B. [2S-[2α,3β(Z)]]-3-[[(2-Amino-4-thiazolyl)-[[2-(diphenylmethoxy)-1,1-dimethyl-2-oxoethoxy]imino]acetyl]amino]-2-methyl-4-oxo-1-azetidinesulfonic acid A solution of 10.00 g of (Z)-2-amino-α-[[2-(diphenylmethoxy)-1,1-dimethyl-2-oxoethoxy]imino]-4-thiazoleacetic acid (21.6 mmol) and 3.97 g (Aldrich, 25.9 mmol) of N-hydroxybenzotriazole hydrate ("HOBt") in 27 ml of DMF was cooled to −3° C., and a solution of 4.68 g (Aldrich, 22.68 mmol) of dicyclohexylcarbodiimide ("DCC") in 10 ml of DMF was added. After stirring at room temperature for 0.5 hour, the yellow suspension was cooled to 0° C., and a solution of 4.08 g (22.68 mmol) of title A compound and 3.16 ml (22.68 mmol) of triethylamine in 27 ml of DMF was added. The reaction was stirred for 2.3 hours at room temperature, and then was cooled to 10° C. To the suspension was added a solution of 10.00 g of (Z)-2-amino-α-[[2-(diphenylmethoxy)-1,1-dimethyl-2-oxoethoxy]imino]-4-thiazoleacetic acid in 27 ml of DMF, followed by a solution of 4.68 g of DCC in 10 ml of DMF. After stirring for 0.5 hour at room temperature, the reaction was charged with a solution of 4.08 g of title A compound and 3.16 ml of triethylamine in 27 ml of DMF. The reaction was then stirred at room temperature.

Twenty hours later, any excess DCC was discharged by the addition of a solution of 0.28 g (2.16 mmol) of oxalic acid dihydrate in 16 ml of H$_2$O. After stirring 10 minutes, the resulting suspension was filtered, and the white precipitate was washed with 2-20 ml portions of DMF. The filtrate was slowly added to 900 ml of chilled dilute HCl (pH 1.40), and 2.0 ml of CH$_3$OH was added to the resulting tan suspension. The precipitate was washed with 120 ml of chilled dilute HCl (pH 1.40), and dried in a vacuum oven overnight at room temperature. The filtrate was stored overnight at room temperature.

The next day a second crop of solid was collected from the filtrate. After vacuum drying at room temperature there was 2.76 g (10.6%) of fluffy white solid. To allow for complete equilibration, the material was stored at ambient conditions for 5 days. The resulting fluffy white solid was identified as the title B compound. By NMR analysis, there was present ca. 0.25 equivalents of DMF and ca. 1.0 equivalents of H$_2$O.

The α-form of [2S-[3α(Z),4β]]-3-[[(2-amino-4-thiazolyl)[(1-carboxy-1-methylethoxy)imino]acetyl]amino]-4-methyl-2-oxo-1-azetidinesulfonic acid which may be used to prepare the corresponding δ-form can be prepared as described in the following Preparation B, in which all temperatures are in degrees Centigrade:

PREPARATION B

α-Form of [3S-[3α(Z),4β]]-3-[[(2-Amino-4-thiazolyl)[(1-carboxy-1-methylethoxy)imino]acetyl]amino]-4-methyl-2-oxo-1-azetidinesulfonic Acid A. N-Benzyloxy-t-boc-threonine amide A solution of 8.76 g of t-boc-threonine and the free amine from 6.4 g of O-benzylhydroxylamine HCl (ethyl acetate-sodium bicarbonate liberation) in 100 ml of tetrahydrofuran was treated with 6.12 g of N-hydroxybenzotriazole and 8.24 g of dicyclohexylcarbodiimide in 20 ml of tetrahydrofuran. The mixture was stirred under nitrogen for 26 hours, filtered, and evaporated in vacuo. The residue was chromatographed on a 300 g silica gel column (elution with chloroform and chloroformethyl acetate (3:1)) yielding 7.2 g of compound. Crystallization from ether-hexane gave 4.18 g of the title compound.

B. (3S-trans)-N-Benzyloxy-3-t-butoxycarbonylamino-4-methylazetidinone

A solution of 12.67 g of N-benzyloxy-t-boc-threonine amide, 11.5 g of triphenylphosphine, and 6.23 ml of diethylazodicarboxylate in 380 ml of tetrahydrofuran was stirred under nitrogen for about 16 hours. The solution was evaporated and chromatographed on a 900 gram silica gel column. Elution with chloroform-ethyl acetate (3:1) gave 13.69 g of compound that crystallizes from ether-hexane to give 9.18 g of the title compound.

C. (3S-trans)-3-t-Butoxycarbonylamino-1-hydroxy-4-methylazetidinone

A solution of 9.18 g of (3S-trans)-N-benzyloxy-3-t-butoxycarbonylamino-4-methylazetidinone in 300 ml of 95% ethanol was stirred in an atmosphere of hydrogen with 1.85 g of 10% palladium on charcoal. After 141 minutes the slurry was filtered and evaporated in vacuo. The residue was recrystallized from ether-hexane to yield 5.12 g of the title compound.

D. (3S-trans)-3-t-Butoxycarbonylamino-4-methylazetidinone

A solution of 4.98 g of (3S-trans)-3-t-butoxycarbonylamino-1-hydroxy-4-methylazetidinone in 200 ml of methanol was treated with 132 ml of 4.5M ammonium acetate and then 66 ml of 1.5M titanium trichloride and stirred for 4.5 hours. The aqueous solution was diluted with an equal volume of 8% sodium chloride and extracted with ethyl acetate to give 3.48 g of crude product. Recrystallization from ether-hexane yielded 3.3 g of the title compound.

E. (3S-trans)-3-Benzyloxycarbonylamino-4-methylazetidinone

A solution of 3.3 g of (3S-trans)-3-t-butoxycarbonylamino-4-methylazetidinone in 10 ml each of dichloromethane and anisole was cooled to 0° C. and 112 ml of trifluoroacetic acid was added. The solution was stirred for 90 minutes and evaporated in vacuo (benzene added and evaporated three times). The residue was dissolved in 70 ml of acetone and the solution was adjusted to pH 7 with 5% sodium bicarbonate solution. A total of 5.33 g of benzyl chloroformate was added over 1 hour at pH 6.5-7.5. The mixture was stirred for 30 minutes at pH 7, diluted with 100 ml of saturated salt, and extracted with ethyl acetate (three 400 ml portions). The residue obtained by evaporation was chromatographed on a 1 liter silica gel column. Elution with chloroform-ethyl acetate (4:1) gave 2.19 g of compound. Crystallization from ether-hexane yielded 1.125 g of the title compound.

F. (3S-trans)-4-Methyl-2-oxo-3-[[(phenylmethoxy)carbonyl]amino]-1-azetidinesulfonic acid, tetrabutylammonium salt A solution of 600 mg of (3S-trans)-3-benzyloxycarbonylamino-4-methylazetidinone in 2 ml of dimethylformamide was cooled to 0° C. and 4 ml of 0.8M sulfur trioxide in dimethylformamide was added. The solution was stirred at room temperature under nitrogen for 1 hour and poured into 80 ml of cold 0.5M monobasic potassium phosphate (adjusted to pH 5.5). The solution was extracted with three 50 ml portions of methylene chloride (discarded) and 868 mg of tetrabutylammonium bisulfate was added. The resulting solution was extracted with four 75 ml portions of methylene chloride. The combined organic layer was washed with 8% aqueous sodium chloride, dried, and evaporated in vacuo yielding 1.54 g of the title compound.

G. [3S-[3α(Z),4β]]-3-[[(2-Amino-4-thiazolyl)[(1-diphenylmethoxycarbonyl-1-methylethoxy)imino]acetyl]amino]-4-methyl-2-oxo-1-axetidinesulfonic acid, potassium salt A solution of 1.54 g of (3S-trans)-4-methyl-2-oxo-3-[[(phenylmethoxy)carbonyl]amino]-1-azetidinesulfonic acid, tetrabutylammonium salt in 45 ml of dimethylformamide was stirred in an atmosphere of hydrogen with 800 mg of 10% palladium on charcoal for 2 hours. The catalyst was filtered and the filtrate stirred for about 16 hours with 1.24 g of (Z)-2-amino-α-[(1-diphenylmethoxycarbonyl-1-methylethoxy)imino]-4-thiazoleacetic acid, 0.4 g of N-hydroxybenzotriazole, and 580 mg of dicyclohexylcarbodiimide. The slurry was evaporated in vacuo and the residue was triturated with 20 ml of acetone and filtered. The filtrate (plus 2 ml of washings) was treated with 868 mg of potassium perfluorobutanesulfonate in 3 ml of acetone. Dilution with 75 ml of ether gave a solid that was isolated by decanation of the mother liquor, trituration with ether, and filtration to give 0.91 g of the title compound. The mother liquor was diluted with a further 100 ml of ether to give a second crop, 0.45 g, of the title compound.

H. [3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid, dipotassium salt A slurry of 140 mg of [3S-[3α(Z),4β]]-3-[[(2-amino-4-thiazolyl)[(1-diphenylmethoxycarbonyl-1-methylethoxy)imino]acetyl]amino]-4-methyl-2-oxo-1-azetidinesulfonic acid, potassium salt (first crop) in 0.5 ml of anisole was stirred at −12° C. under nitrogen and 2.5 ml of cold (−10° C.) trifluoroacetic acid was added. After 10 minutes, 10 ml of ether and 5 ml of hexane were added and the resulting slurry was stirred for 5 minutes at −12° C., and allowed to warm to room temperature. The solid was isolated by centrifugation and washed twice with ether. A solution of this solid in 5 ml of cold water was immediately adjusted to pH 5.5 with 0.4N potassium hydroxide and then applied to an 80 ml HP-20AaG column. Elution with water gave 72 mg of the title compound in fractions (10 ml) 7–11 after evaporation (acetonitrile added and evaporated three times) and trituration with ether. Analysis calc'd for $C_{13}H_{15}N_5O_8S_2K_2$: C, 30.51; H, 2.95; N, 13.69; S, 12.53; K, 15.28; Found: C, 29.63; H, 3.20; N, 12.96; S, 11.94; K, 12.78.

The remaining 1.22 g of [3S-[3α(Z),4β]]-3-[[(2-amino-4-thiazolyl)[(1-diphenylmethoxycarbonyl-1-methylethoxy)imino]acetyl]amino]-4-methyl-2-oxo-1-azetidinesulfonic acid, potassium salt (crops 1 and 2) were treated as above (4.2 ml anisole, 16 ml of trifluoroacetic acid, 13 minutes at −15° C.). Chromatography on a 300 ml HP-20AG column gave 694 mg of the title compound in fractions (60 ml) 6–9 after treatment as above.

I. α-Form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid, dipotassium salt (87.3 mg) was dissolved in 1.38 ml of water, cooled to 0° C., treated with 0.34 ml of 1N hydrochloric acid and the resulting crystals separated by centrifugation. The wet solid was dissolved in methanol, filtered, concentrated to above 0.5 ml and mixed with 1 ml of water, giving 55.9 mg of the title compound.

The following Examples represent preferred embodiments of the present invention. All temperatures are expressed in degrees Centigrade.

EXAMPLES 1 AND 2

δ-Form of
[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (Preparation of Title Compound by Trifluoroacetic Acid—Mediated Solvolysis of [2S-[2α,3β(Z)]]-3-[[(2-Amino-4-thiazolyl)-[[2-(diphenylmethoxy)-1,1-dimethyl-2-oxoethoxy]imino]acetyl]amino]-2-methyl-4-oxo-1-acetidinesulfonic acid)

EXAMPLE 1

A solution of 40.0 ml of anisole in 160 ml of $CH_2Cl_2$ was chilled to 0° C., and 60.17 g of [2S-[2α,3β(Z)]]-3-[[(2-amino-4-thiazolyl)-[[2-(diphenylmethoxy)-1,1-dimethyl-2-oxoethoxy]imino]acetyl]amino]-2-methyl-4-oxo-1-azetidinesulfonic acid was added. With further cooling, 100 ml of trifluoroacetic acid was added and the reaction was stirred at 0°–5° C. for 1.5 hours. The reaction was transferred into a solution of 4.5 ml $H_2O$ in 225 ml of anhydrous acetone-denatured alcohol (SDA-23A) (100:8 absolute ethanol:acetone). The resulting suspension was chilled, and the solids were collected by filtration and washed with $CH_2Cl_2$. Vacuum drying without heat afforded 41.7 g of the title compound in the form of a dense, slightly yellow solid.

Crystal form: δ-form (X-ray powder diffraction).
Solvation: 11.6% $CH_2Cl_2$ (GC analysis).
$H_2O$ content: 3.08% (Karl Fischer titration).
HPLC purity: 76.9% (80.9% theo.).

EXAMPLE 2

A solution of 40.0 ml of anisole in 160 ml of $CH_2Cl$ was cooled to −2° C., and 60.17 g of [2S-[2α,3β(Z)]]-3-[[(2-amino-4-thiazolyl)-[[2-(diphenylmethoxy)-1,1-dimethyl-2-oxoethoxy]imino]acetyl]amino]-2-methyl-4-oxo-1-azetidinesulfonic acid was added. Next 100 ml of TFA was added slowly enough so that the reaction temperature did not exceed 5° C. The reaction was stirred at 2°–3° C. for 1.5 hours, and then the reaction was poured into a room temperature solution composed of 220 ml of absolute EtOH, 17.6 ml of acetone, and 11.8 ml of $H_2O$. The resulting slurry was stirred at room temperature for 20 minutes, and then chilled in crushed ice for 20 minutes. The precipitate was filtered off and washed with two 100 ml portions of $CH_2Cl_2$. Vacuum drying returned 37.83 g of dense white solid.

Crystal form: δ form of aztreonam (X-ray powder diffraction).
Solvation: 15.6% $CH_2Cl_2$, 1.5% EtOH (GC analysis).
$H_2O$ content: 3.79% (Karl Fischer titration).
HPLC purity: 79.8%.

EXAMPLES 3 AND 4

δ-Form of
[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (Preparation of Title Compound by Ttrichloroacetic Acid—Mediated Solvolysis of [2S-[2α,3β(Z)]]-3-[[(2-Amino-4-thiazolyl)-[[2-(diphenylmethoxy)-1,1-dimethyl-2-oxoethoxy]imino]acetyl]amino]-2-methyl-4-oxo-1-acetidinesulfonic acid)

EXAMPLE 3

A solution of 4.0 ml of anisole in 20 ml of $CH_2Cl_2$ was chilled to 3°–5° C., and 6.0 g of [2S-[2α,3β(Z)]]-3-[[(2-amino-4-thiazolyl)-[[2-(diphenylmethoxy)-b 1,1-dimethyl-2-oxoethoxy]imino]acetyl]amino]-2-methyl-4-oxo-1-azetidinesulfonic acid was added. After the addition of a solution of 16.4 g of TCA in 20 ml of $CH_2Cl_2$, the solution was warmed to 28° C., and held at 25°–27° C. for 0.5 hour. Then the reaction was cooled to 15°–18° C., and quenched by the addition of 0.3 ml of $H_2O$ in 30 ml of absolute EtOH. The mixture was chilled and filtered, and the precipitate was washed with $CH_2Cl_2$.

Vacuum drying afforded 3.94 g of the title compound in the form of off-white solid.
  Crystal form: δ-form (X-ray powder diffraction).
  Solvation: 9.2% $CH_2Cl_2$, 90.7% EtOH (GC analysis).
  $H_2O$ content: 3.77% (Karl Fischer titration).
  HPLC purity: 74.8% (80.9% theo.).

EXAMPLE 4

A solution of 16.4 g of trichloroacetic acid and 4.0 ml of anisole in 46 ml of $CH_2Cl_2$ was cooled to 14° C., and 6.0 g of [2S-[2α,3β(Z)]]-3-[[(2-amino-4-thiazolyl)-[[2-(diphenylmethoxy)-1,1-dimethyl-2-oxoethoxy]imino]acetyl]amino]-2-methyl-4-oxo-1-azetidinesulfonic acid was added. The suspension was warmed to 32° C., and was then allowed to stir at 23° C. for 40 minutes. After quenching with a solution of 0.3 ml of $H_2O$ and 2.2 ml of acetone in 27.8 ml of EtOH, the slurry was stirred 1 hour at 23° C. The suspension was cooled to 3° C., and the solids were washed with 30 ml of $CH_2Cl_2$. Drying under reduced pressure returned 4.0 g of white solid.
  Crystal form: δform of aztreonam (X-ray powder diffraction).
  Solvation: 12.9% $CH_2Cl_2$, 1.1% EtOH (GC analysis).
  $H_2O$ content: 3.19% (Karl Fischer titration).
  HPLC purity: 76.1%.

EXAMPLE 5

Recrystallization of δ-For of [3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid A solution of 5.00 g of the δ-form of aztreonam (prepared as described in Example 1) in 7.5 ml of DMSO was polish filtered, and the filtrate was added dropwise over 5 minutes to 200 ml of $CH_2Cl_2$. After stirring at room temperature for 0.5 hour, the suspension was chilled at 3°-5° C. The resulting white crystalline solids were filtered off and washed with $CH_2Cl_2$. Vacuum drying afforded 4.45 g of the title compound in the form of white crystals.
  Crystal form: δ-form (X-ray powder diffraction).
  Solvation: 8.9% $CH_2Cl_2$ (GC analysis).
  $H_2O$ content: 3.89% (Karl Fischer titration).
  HPLC purity: 73.7%.

EXAMPLE 6

Recrystallization of α-Form of Aztreonam to δ-Form

A solution of 5.00 g of the α-form of aztreonam in 7.5 ml of DMF was polished filtered and diluted with 3.4 ml of DMF. Then 20 ml of $CH_2Cl_2$ was added in portions, and the solution was allowed to stand at room temperature for 2 hours. The resulting suspension was chilled 1 hour, and the solids were washed with $CH_2Cl_2$. Vacuum drying returned 4.31 g of the title compound in the form of a white solid.
  Crystal form: δ-form (X-ray powder diffraction).
  Solvation: 9.6% $CH_2Cl_2$ (GC analysis).
  $H_2O$ content: 3.50% (Karl Fischer titration).
  HPLC purity: 79.2%.

EXAMPLE 7

To a 12° C. solution of 20 ml of anisole and 82.0 g of trichloroacetic acid (TCA) in 230 ml of $CH_2Cl_2$ was added 30.08 g of [2S-[2α,3β(Z)]]-3-[[(2-amino-4-thiazolyl)-[[2-(diphenylmethoxy)-1,1-dimethyl-2-oxoethoxy]imino]acetyl]amino]-2-methyl-4-oxo-1-azetidinesulfonic acid and the reaction was stirred at 15°-20° C. for 1.75 hours. Then the reaction was quenched by the addition of 150 ml of SD-3A ethanol (95:5:5 ethanol:$H_2O$:methanol). With vigorous stirring the sticky mass that was formed initially became a heavy white suspension, and after 1.5 hours at room temperature the suspension was cooled. The product was filtered off and washed with $CH_2Cl_2$. Vacuum drying returned 18.41 g of white solid.
  Crystal form: δ-form of aztreonam (X-ray powder diffraction).
  Solvation: 13.88% $CH_2Cl_2$ and 1.3% EtOH (GC analysis).
  $H_2O$ content: 3.11% (Karl Fischer titration)
  HPLC purity: 76.9% (80.9% theo.)

EXAMPLE 8

Recrystallization of β-Form of Aztreonam to δ-Form

A 250 g sample of the β-form of aztreonam was dissolved in a mixture of 1.59 l of $H_2O$ and 2.66 l of ethanol at 60° C., and the solution was allowed to cool slowly for 4 hours. The mixture was then chilled for 1.5 days, and the product was filtered off. Vacuum drying at 30° C. returned 258 g of white solid, which was then dissolved in 386 ml of dimethyl formamide. The solution was polish filtered, and to the filtrate was added 1.0 l of $CH_2Cl_2$ over 30 minutes. After stirring at 27° C. for 0.5 hours, the crystalline suspension was diluted with 0.54 l of $CH_2Cl_2$, and chilled for 5 hours. The dense white product was filtered off and washed with $CH_2Cl_2$. Drying returned 275.1 g of dense white solid.
  Crystal form: δ-form of aztreonam (X-ray powder diffraction).
  Solvation: 16% $CH_2Cl_2$ (GC analysis).
  $H_2O$ content: 4.32% (Karl Fischer titration).
  HPLC purity: 79.1% (80.9% theo.).

What is claimed is:

1. The delta (δ)-form of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid.

2. The compound of claim 1 comprised of aztreonam, from about 9 to about 16% by weight $CH_2Cl_2$ and from about 2.5 to about 4.5% by weight water.

3. The compound of claim 2 comprised of a 1:1:1 (molar) complex of aztreonam:$CH_2Cl_2$:$H_2O$.

4. The compound of claim 2 comprised of aztreonam, 15.8% by weight $CH_2Cl_2$ and 3.35% by weight $H_2O$.

5. The method of preparing the compound as defined in claim 1, which comprises dissolving [2S-[2α,3β(Z)]]-3-[[(2-amino-4-thiazolyl)-[[2-(diphenylmethoxy)-1,1-dimethyl-2-oxoethoxy]imino]acetyl]amino]-2-methyl-4-oxo-1-azetidinesulfonic acid in $CH_2Cl_2$, reacting the mixture with an acid and then mixing the reaction mixture with water.

6. Tthe method as defined in claim 5 wherein the acid is trifluoroacetic acid or trichloroacetic acid.

7. The method of preparing the compound as defined in claim 1, which comprises dissolving the α-form of aztreonam in an anhydrous organic polar solvent, adding $CH_2Cl_2$ and crystallizing the δ-form of aztreonam therefrom.

8. The method as defined in claim 1 wherein said organic polar solvent is dimethylformamide or dimethylsulfoxide.

9. The method of preparing the compound as defined in claim 1, which comprises dissolving an acid in a chlorinated hydrocarbon solvent therefor which is $CH_2Cl_2$, and reacting the solution with [2S-[2α,3β(Z)]]-3-[[(2-amino-4-thiazolyl)-[[2-(diphenylmethoxy)-1,1-methyl-2-oxoethoxy]imino]acetyl]amino]-2-methyl-4-1-azetidinesulfonic acid.

10. The method as defined in claim 9 wherein the acid is trichloroacetic acid or trifluoroacetic acid.

11. The method of preparing the compound as defined in claim 1, which comprises dissolving the β-form of aztreonam in a solvent therefor, cooling the resulting solution to precipitate a solid, separating the solid from the mixture, dissolving the solid in an organic polar solvent, adding a chlorinated hydrocarbon solvent which is $CH_2Cl_2$ and crystallizing the δ-form of aztreonam therefrom.

12. The method of claim 11 wherein the polar organic solid is dimethylformamide or dimethylsulfoxide.

* * * * *

UNITED STATES PATENT AND TRADEMARK OFFICE
CERTIFICATE OF CORRECTION

PATENT NO. : 4,826,973
DATED : May 2, 1989
INVENTOR(S) : Neal G. Anderson; Carl F. Anderson It is certified that error appears in the above-identified patent and that said Letters Patent is hereby corrected as shown below:

Claim 9, next to last line, change "4-1" to --4-oxo-1--.

Signed and Sealed this

Third Day of October, 1989

Attest:

DONALD J. QUIGG

Attesting Officer     Commissioner of Patents and Trademarks